(12) United States Patent
Hauger et al.

(10) Patent No.: US 9,615,740 B2
(45) Date of Patent: Apr. 11, 2017

(54) EYE SURGERY MICROSCOPE HAVING AN ENTITY FOR MEASURING AN AMETROPIA

(71) Applicants: Carl Zeiss Meditec AG, Jena (DE);
Carl Zeiss AG, Oberkochen (DE)

(72) Inventors: Christoph Hauger, Aalen (DE);
Markus Seesselberg, Aalen (DE);
Marco Wilzbach, Stuttgart (DE)

(73) Assignees: CARL ZEISS MEDITEC AG, Jena (DE); CARL ZEISS AG, Oberkochen (DE)

( * ) Notice: Subject to any disclaimer, the term of this patent is extended or adjusted under 35 U.S.C. 154(b) by 36 days.

(21) Appl. No.: 14/579,053

(22) Filed: Dec. 22, 2014

(65) Prior Publication Data
US 2015/0109580 A1 Apr. 23, 2015

Related U.S. Application Data

(63) Continuation of application No. PCT/EP2013/001794, filed on Jun. 18, 2013.

(30) Foreign Application Priority Data

Jun. 21, 2012 (DE) .......................... 10 2012 012 281

(51) Int. Cl.
*A61B 3/14* (2006.01)
*A61B 3/13* (2006.01)
(Continued)

(52) U.S. Cl.
CPC ............... *A61B 3/13* (2013.01); *A61B 3/102* (2013.01); *A61B 3/14* (2013.01); *A61B 90/20* (2016.02); *G02B 21/0012* (2013.01)

(58) Field of Classification Search
CPC .................................... A61B 3/12; A61B 3/14
(Continued)

(56) References Cited

U.S. PATENT DOCUMENTS 5,867,308 A   2/1999  Pensel et al.
6,419,671 B1  7/2002  Lemberg
(Continued)

FOREIGN PATENT DOCUMENTS

DE    10 2005 022 125 A1   11/2006
DE    10 2008 011 608 A1    9/2009
(Continued)

OTHER PUBLICATIONS

International Search Report issued in corresponding International application No. PCT/EP2013/001794, date of mailing Sep. 13, 2013.
(Continued)

*Primary Examiner* — James Greece
(74) *Attorney, Agent, or Firm* — Patent Portfolio Builders PLLC

(57) ABSTRACT

An eye surgery microscope 1 having an illumination beam path 9 for imaging a portion of an eye 3 of a patient and a measurement beam path 25 for measuring an ametropia of the eye. The microscope comprises an objective lens 11 having an objective plane 13 in which the eye of the patient is disposable; at least one ocular 17 or a camera 19 for generating and detecting an image of the object plane, respectively; a measurement light source for generating a measurement light beam 29; a measurement module 41 having a light detector; optics traversed by the measurement beam path for directing the measurement light beam onto the retina 7 of the eye of the patient and for providing measurement light 39 reflected at the retina to the measurement module; and a controller; wherein the measurement module and the controller are configured to determine a position of an image of the retina generated by the optics along the measurement beam path and to output a measurement value representing the ametropia of the eye of the patient.

18 Claims, 13 Drawing Sheets

(51) Int. Cl.
*G02B 21/00* (2006.01)
*A61B 3/10* (2006.01)
*A61B 90/20* (2016.01)

(58) Field of Classification Search
USPC .............................. 351/200, 205, 206, 246
See application file for complete search history.

(56) References Cited

U.S. PATENT DOCUMENTS

| | | |
|---|---|---|
| 2005/0018134 A1 | 1/2005 | Noda et al. |
| 2008/0234972 A1 | 9/2008 | Tsukada et al. |
| 2009/0219483 A1 | 9/2009 | Takanashi et al. |
| 2009/0257065 A1 | 10/2009 | Hauger et al. |
| 2010/0194757 A1* | 8/2010 | Tomidokoro et al. ........ 345/440 |
| 2012/0069303 A1 | 3/2012 | Seesselberg et al. |
| 2012/0092615 A1 | 4/2012 | Izatt et al. |
| 2012/0140173 A1 | 6/2012 | Uhlhorn et al. |
| 2013/0076960 A1 | 3/2013 | Bublitz et al. |
| 2013/0135585 A1 | 5/2013 | Heiberger et al. |

FOREIGN PATENT DOCUMENTS

| | | |
|---|---|---|
| DE | 10 2008 047 400 B4 | 7/2010 |
| DE | 10 2010 010 569 A1 | 9/2011 |
| DE | 10 2010 024 606 A1 | 12/2011 |
| DE | 10 2012 083 353 A1 | 3/2013 |
| EP | 2 103 249 A1 | 9/2009 |
| EP | 2 443 991 A1 | 4/2012 |
| WO | 96/13743 A1 | 5/1996 |

OTHER PUBLICATIONS

German Office Action, with translation thereof, in corresponding German Application No. 10 2012 012 281.0 dated Apr. 29, 2013.
U.S. Appl. No. 14/577,235, entitled Apparatus for Determining an Ametropia of an Eye filed Dec. 19 2014.

* cited by examiner

EYE SURGERY MICROSCOPE HAVING AN ENTITY FOR MEASURING AN AMETROPIA

CROSS-REFERENCES TO RELATED APPLICATIONS

The present application is a continuation of International application no. PCT/EP2013/001794, which claims priority from, German Patent Application No. 10 2012 012 2819.0, filed on Jun. 21, 2012 and entitled, "Ophthalmic Surgery Microscope Comprising a Device for Measuring Refractive Errors (Ametropia)," the contents of these two documents is hereby incorporated by reference in their entirety.

FIELD

The invention relates to a microscope for usage in eye surgery wherein the microscope provides an imaging beam path for imaging a portion of an eye of a patient and a measurement beam path for measuring an ametropia of the eye.

BACKGROUND

EP 2 103 249 A1 discloses an eye surgery microscope comprising an entity for measuring an ametropia of an inspected eye of a patient. The entity for measuring the ametropia comprises a wavefront sensor for analyzing wavefronts of light emerging from the eye and to determine the ametropia of the eye based on the analyzed wavefronts. The wavefront sensor is a Hartmann-Shack-sensor.

Indeed, the ametropia of the inspected eye can be determined relatively well with respect to multiple parameters using such a wavefront sensor, however, the wavefront sensor is expensive and requires a relatively large installation space and, therefore, may not be easily integrated into the microscope and further is sensitive to stray light.

SUMMARY

Accordingly, it is an objective of the present invention to propose an eye surgery microscope having a simplified entity for measuring the ametropia of the inspected eye.

According to embodiments of the invention, an eye surgery microscope is proposed in which, for measuring the ametropia of the inspected eye, a measurement light beam is directed onto the inspected eye in a way that a small spot on the retina of the eye is illuminated by the measurement light beam. A portion of the measurement light is reflected by the retina and provided to a measurement module by optics. The optics are configured in a way that an image of the retina is formed into the measurement module so that the illuminated spot on the retina is imaged in the measurement module. The position of the image plane of the retina depends on the refractive power of the lens and, therefore, on the ametropia of the eye. The microscope is configured to determine the position of this image plane along the beam path of the reflected measurement light and to determine a measurement value representing the ametropia of the eye, based on the position.

According to exemplary embodiments, a microscope for usage in eye surgery is proposed providing an imaging beam path for imaging a portion of an eye of a patient and a measurement beam path for measuring an ametropia of the eye of the patient, and wherein the microscope comprises: an objective lens traversed by the imaging beam path and having an object plane in which the eye of the patient is disposable, at least one of at least one ocular disposed in the imaging beam path behind the objective lens for generating an image of the object plane and a camera disposed in the imaging beam path behind the objective lens for detecting an image of the object plane, a measurement light source for generating a measurement light beam, a measurement module disposed in the measurement beam path and having at least one light detector detecting measurement light, optics traversed by the measurement beam path for directing the measurement light beam onto a retina of the eye of the patient and for providing measurement light reflected at the retina to the measurement module, and a controller, wherein the measurement module and the controller are configured to determine a position of an image of the retina along the measurement beam path, wherein the image of the retina is generated by the optics, and to output a measurement value representing the ametropia of the eye of the patient.

According to some embodiments, a possibility for measuring the position of the image of the retina generated by the optics along the measurement beam path is provided in that the microscope comprises a drive for displacing a position of at least one component disposed in the measurement beam path in a direction of the measurement beam path, wherein the at least one light detector provides a detection signal representing an illumination strength of the measurement light incident onto the at least one light detector, and wherein the controller is configured to control the drive in dependence of the detection signal until the illumination strength of the measurement light incident onto the at least one light detector fulfils a predetermined condition, and wherein the controller is configured to then output the measurement value representing the ametropia of the eye of the patient in dependence of an obtained position of the at least one component.

The measurement light reflected by the retina is provided to the measurement module by the optics as a beam. As the measurement light emerges from a small spot on the retina, the cross-section of this beam will have a minimum cross-section in the plane in which the image of the retina and, therefore, the image of the spot is formed. The diameter of this beam will be larger with increasing distance from the image plane in the beam path before and behind the image plane. Accordingly, the illumination strength within the beam, i.e., the light power per unit area, for example measured in watts per square meter, will be at maximum in the plane of the image and decrease with increasing distance along the beam path. Therefore, the position of the image of the retina may be concluded from measuring the illumination strength within the beam.

According to exemplary embodiments herein, the component disposed in the measurement beam path and the position of which is displaceable by the drive comprises the at least one light detector. The at least one light detector may then be displaced by the drive in order to find the position of the light detector where the illumination strength of the measurement light incident onto the light detector is at maximum. Then, this position corresponds to the position of the image of the retina wherein this position depends on the ametropia of the eye which, in turn, may therefore be determined based on the obtained position of the image. Therefore, the predetermined condition is then fulfilled if the illumination strength of the measurement light incident onto the at least one light detector is at maximum.

According to further embodiments, the component disposed in the measurement beam path and the position of which is displaceable by the drive is a lens of the optics traversed by the measurement beam path. With this, the position of the image of the retina is displaced along the measurement beam path by displacing the lens. If the light detector is disposed in the measurement beam path at a fixed position, the position of the lens may be changed by the drive controlled by the controller until the illumination strength detected by the light detector is at maximum, which is then the case if the image plane of the retina coincides with the detection cross-section of the detector. The position of the lens necessary for this depends on the ametropia of the eye so that, in turn, the ametropia of the eye may be determined based on the position of lens. Also, the predetermined condition may then be fulfilled if the illumination strength of the measurement light incident onto the at least one light detector is at maximum. Beside this condition, also other conditions exist. For example, the component disposed in the measurement beam path may be displaced in a direction of the measurement beam path to multiple mutually different positions, at each position, the illumination strength may be measured, and then, based on the different measurement values of the illumination strength and by a suitable calculation method such as interpolation, it can be determined at which position the image plane of the retina is located in the beam path.

According to further exemplary embodiments, the measurement module comprises two light detectors disposed along the measurement beam path at different distances from the object plane, wherein the predetermined condition is fulfilled if the illumination strengths of the measurement light incident onto the light detectors have a predetermined ratio, and in particular are equal. The displaceable component is then preferably displaced by the drive along the measurement beam path in a way that one of the two detectors is disposed in the beam path before the image of the retina and the other one of the two detectors is disposed behind the image of the retina. Based on the ratio of the illumination strengths detected by the light detectors, the position of the image of the retina relative to the two detectors in the beam path may then be determined. If the measured illumination strengths are equal, for example, the image of the retina is located in the center between the two light detectors. The measurement light may be provided simultaneously to the two light detectors by a beam splitter, for example.

According to further exemplary embodiments, the measurement module has a plurality of light detectors detecting the measurement light, wherein the light detectors of the plurality of light detectors are disposed along the measurement beam path at different distances from the object plane and wherein each of the light detectors of the plurality of light detectors provides a detection signal representing the measurement light incident onto the respective light detector, and wherein the controller is configured to output the measurement value representing the ametropia of the eye of the patient in dependence of the detection signals.

According to exemplary embodiments herein, the measurement module comprises an astigmatic lens, in particular a cylinder lens, focusing the measurement light emerging from the spot on the retina along a line. Accordingly, the plurality of light detectors may be disposed in way that their distance from the object plane increases in direction of the line of the line focus so that multiple light detectors are simultaneously illuminated by measurement light. Those light detectors, disposed along the line at the position of the measurement beam path where the image of the retina is formed for a given ametropia of the eye of the patient, will detect a maximum illumination strength so that the ametropia of the inspected eye of the patient may be concluded based on this position.

According to exemplary embodiments, the plurality of light detectors is provided by a two-dimensional array of light detectors. According to alternative exemplary embodiments, the plurality of light detectors is provided by a line-detector, the individual light detectors of which are disposed along a straight line.

According to exemplary embodiments, the measurement light beam is directed onto the retina of the eye by the optics in a way that the measurement light beam has, in the object plane of the objective lens, a diameter of less than 3.5 mm, in particular less than 2.5 mm and more in particular less than 1.5 mm. For this, a lower limit of the diameter of the measurement light beam may amount to 0.5 mm. Using such a small diameter of the measurement light beam, an accordingly small diameter of the spot on the retina illuminated by the measurement light may be obtained, even if the refractive power of the eye lens strongly differs from the refractive power of a normal eye.

According to exemplary embodiments, the measurement beam path traverses the objective lens, wherein, then, a mirror disposed on the side opposite to the side of the object plane respect to the objective lens may be provided in order to superimpose the measurement beam path with the imaging beam path of the microscope.

Such a mirror may also be disposed between the objective lens and the objective plane, wherein, then, the measurement light beam does not traverse the objective lens.

According to certain exemplary embodiments, the light detector has a detection cross-section being which is smaller than a diameter of the beam of measurement light incident onto the detection cross-section, reflected at the retina and provided to the measurement module so that the detected light energy represents the illumination strength, i.e. the light power per unit area. If the detection cross-section was greater than the diameter of the beam, the detector would detect the full power of the beam and not the illumination strength in the beam.

A minimum diameter of the beam of measurement light incident onto the detection cross-section, reflected at the retina and provided to the measurement module may be estimated based on a diameter of the measurement light beam incident onto the retina in the plane of the eye lens and the pupil of the eye, respectively: assuming that the diameter of the measurement light beam directed onto the eye amounts to 1 mm in the plane of the eye lens and that the refractive power of the eye lens towards the retina amounts to typically 22 mm, then, the measurement light is incident onto the retina at a divergence angle $\Theta$ being equal to half the diameter of the beam divided by the focal length of the eye. Using the assumed amounts, the divergence angle $\Theta$ amounts to 22.7 mrad. Using the assumption that the measurement light beam is a Gaussian bundle, the radius of the beam bundle on the retina may be calculated as wavelength of the light divided by pi divided, by a refractive index of the glass body divided, by the above given, divergence. Using, the assumption that the refractive index of the glass body typically amounts to 1.33 and light of a wavelength of 0.84 µm is used, a radius and a diameter of the spot illuminated by the measurement light on the retina amounts to 9 µm and 18 µm, respectively. This estimation is valid for an ideal eye. However, depending on the ametropia of the patient, the diameter may be 10 times greater.

The spot illuminated on the retina is imaged into the measurement module by the optics disposed in the beam path between the retina and measurement module. An imaging magnification β may be assigned to this imaging. The diameter of the beam of measurement light incident onto the detection cross-section, reflected at the retina and provided to the measurement module is, therefore, equal to the diameter of the spot illuminated by measurement light on the retina multiplied by the imaging magnification β of said optics.

The detection cross-section may be defined by a recess in an aperture disposed in the beam path before the light detector. However, the detection cross-section may also be defined by an area of a light sensitive substrate of the detector itself.

According to exemplary embodiments, a first end of a light guide such as a glass fiber is disposed in the beam path wherein measurement light enters the light guide at the first end and is guided to the light detector. Then, the cross-section of the light guide defines the detection cross-section of the light detector.

According to exemplary embodiments herein, the light guide is also used to generate, the measurement light, beam wherein the measurement light is coupled into the light guide at a second end of the light guide disposed opposite to the first end of the light guide of via a coupling element such as a beam splitter.

According to further exemplary embodiments, the light guide may be a part of an optical coherence tomography system which may be used to record depth profiles of portions of the eye of the patient and to determine a 3-dimensional structure of the portions or the eye of the patient.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
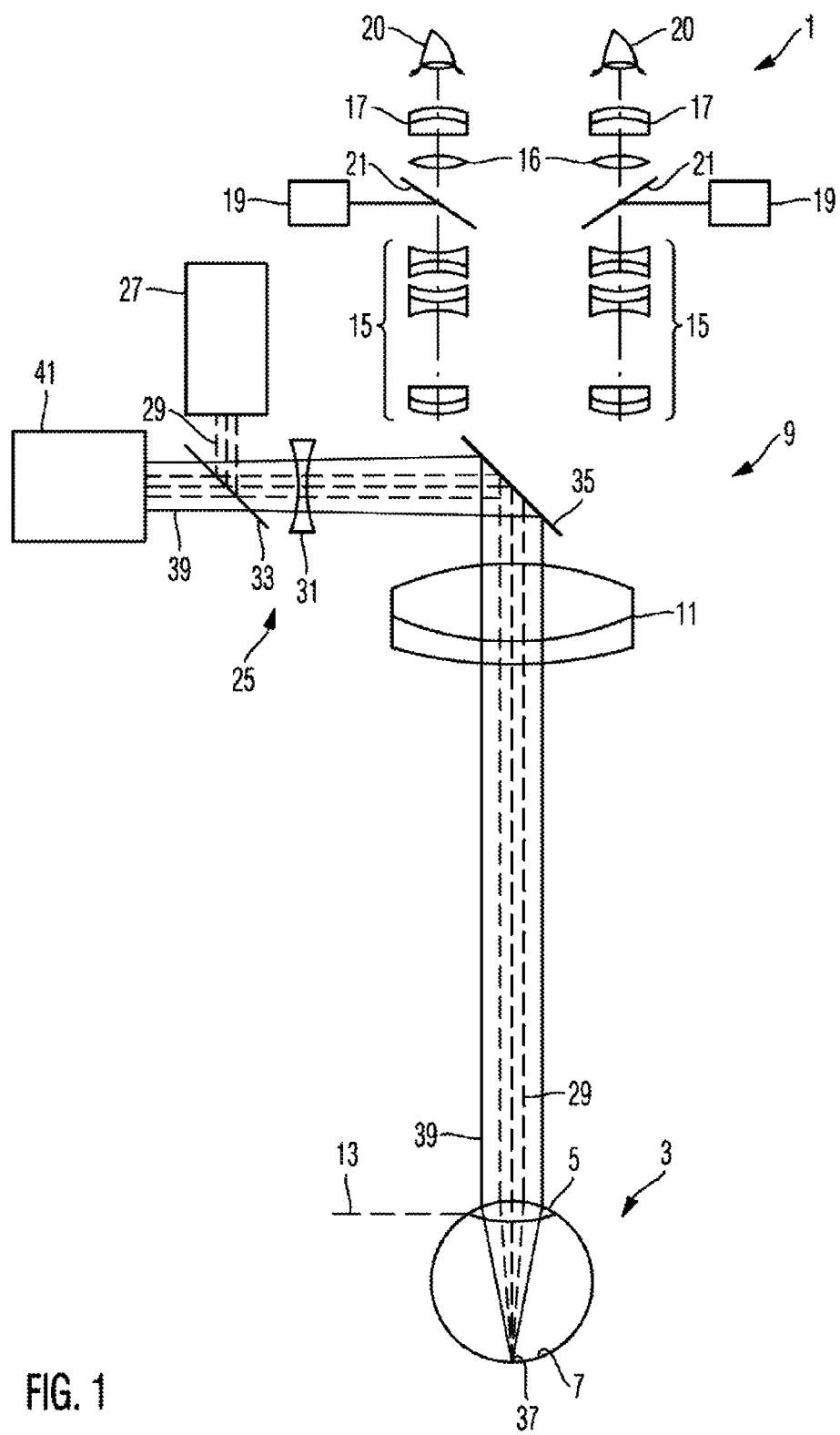
FIG. 1 shows a schematic illustration of an eye surgery microscope according to a first embodiment.

In the exemplary embodiments described below, components that are alike in function and configuration are designated as far as possible by alike reference numerals. Therefore, to understand the features of the individual components of a specific embodiment, the descriptions of other embodiments and of the summary of the disclosure should be referred to.

FIG. 1 is a schematic illustration of an eye surgery microscope 1 for inspecting an eye 3 of a patient. The eye 3 comprises as essential elements for the description of the microscope 1 an eye lens 5 and a retina 7. The microscope 1 has an imaging beam path 9 in order to image portions of the eye 3. An objective lens 11 is disposed in the imaging beam path 9 wherein the portion of the eye to be imaged by the imaging beam path 9 is disposable in an object plane 13 of the objective lens 11. The object plane 13 may be imaged to infinity by the objective lens 11. In pairs, a zoom system 15 for changing a magnification of the imaging, a tube lens 16 and an ocular 17 and a camera 19 are disposed in the imaging beam path behind the objective lens 11. The object plane 13 is imaged onto the image sensor of the camera 19 so that, using the camera 19, an image of the object plane may be recorded. The tube lens 16 and the ocular 17 also generate an image of the object plane which may be viewed by a user using his eye 20. A beam splitter 21 is provided for splitting the beam path between the camera 19 and the ocular 17 so that the user 20 may observe the image of the object plane 13 while the camera 19 records an image of the object plane.

The zoom system 15, the ocular 17 and the camera 19 are provided as pairs in the illustrated embodiment so that stereoscopic images of the eye 3 may be observed and recorded, respectively.

However, it is also possible not to provide in pairs and merely provide one ocular and/or one camera for observing and recording monoscopic images of the object plane 13, respectively. Furthermore, merely one or two cameras and no oculars may be provided for recording only images of the object plane without providing sight through an ocular, and merely one or two oculars and no camera may be provided for observing only the image of the object plane. Furthermore, a zoom system does not need to be provided so that the imaging beam path 9 provides a fixed magnification only.

Furthermore, the microscope 1 provides a measurement beam path 25 for measuring an ametropia of the eye 3. For this, the microscope comprises a measurement light source 27 for generating a measurement light beam 29, optics 31, which are schematically illustrated as a lens in FIG. 1 but may also comprise multiple lenses, and two mirrors 33 and 35 for directing the measurement light beam 29 onto the eye 3 in a way that the measurement light beam 29 illuminates a small spot 37 on the retina 7 of the eye 3. The spot 37 may have a diameter of, for example, less than 1.000 μm less than 200 μm or less than 50 μm. This diameter depends on the wavelength of the measurement light, the diameter of the measurement light beam 29 in the plane of the eye lens 5, the divergence and convergence of the measurement light beam, respectively, and the ametropia of the eye. A portion of the light of the measurement light beam 29 directed onto the spot 37 is reflected at the retina 7 and is emitted from the eye 3 as a beam 39 which is reflected at the mirror 35, traverses the optics 31 and also traverses the partially transparent mirror 33 in order to enter a measurement module 41. The optics 31 are configured in a way that an image of the retina 7 and, therefore, of the illuminated spot 37 is formed in the measurement module. The position of this image along the measurement beam path depends on the refractive power of the eye lens 5 and, therefore, on the ametropia of the eye 3. The measurement module 41 is configured to determine the position of the image of the retina along the measurement beam path and to output a measurement value representing the ametropia of the eye 3.

In the illustrated embodiment, the measurement beam path traverses the objective lens 11. This, however, is not necessary. It is also possible that the measurement beam path does not traverse the objective lens 11 which may be realized in that, for example, the mirror 35 superimposing the measurement beam path 25 with the imaging beam path 9 is disposed between the objective lens 11 and the object plane 13. Also then, the optics 31 may be configured in a way that an image of the retina is formed in the measurement module 41.

Furthermore, it is possible that the measurement light beam 29 generated by the measurement light source 27 traverses the beam splitter 33 and the beam 39 of measurement light reflected at the retina 7 is reflected at the beam splitter 33 in order to enter the measurement module 41.

As the beam 39 of measurement light reflected at the retina 7 has, when leaving the eye 3, a diameter corresponding to the diameter of the pupil of the eye 3, the diameter of the measurement light beam 29 entering the eye may be munch smaller in comparison. For example, the measurement light beam 29 may have, in the object plane 13 and in the plane of the pupil of the eye 3, respectively, a diameter of less than 3.5 mm, less than 2.5 mm and in particular less than 1.5 mm. This is advantageous in order to generate a preferably small illuminated spot 37 on the retina 7, even if the ametropia of the eye 3 is large. Furthermore, then, the optics 31 do not necessarily need to be adapted to the present ametropia of the eye in order to generate a preferably small illuminated spot 37.

A wavelength of the measurement light 29 generated by the measurement light source 27 is preferably in a range of 400 nm to 1500 nm and may also be outside of the visible range in order to avoid dazzling of the patient.

Figure 2:
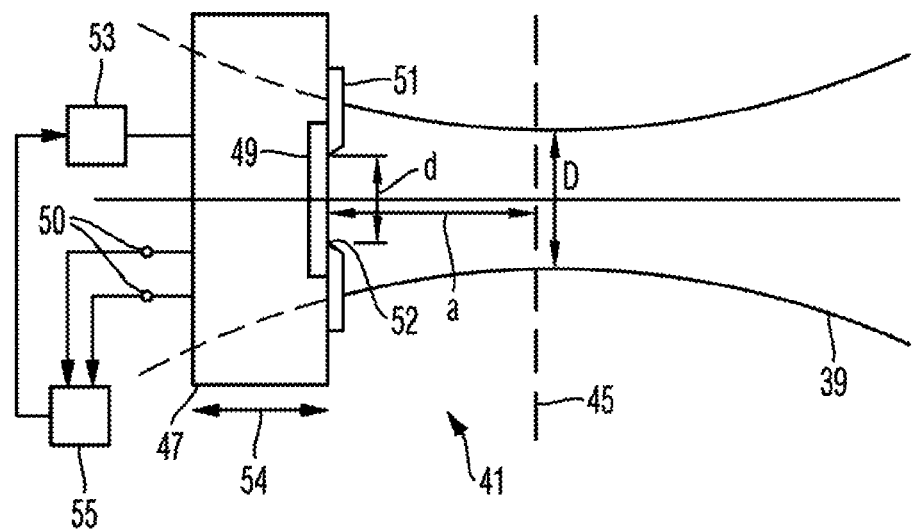
FIG. 2 shows a schematic illustration of a light detector which may be used in a measurement module of an eye surgery microscope.

FIG. 2 shows a detail of the measurement module 41 in which an image of the retina is formed in an image plane 45. A diameter D of the beam 39 is smallest in the image plane 45. At the image plane 45, the beam 39 has a beam waist. The diameter of the beam and, therefore, the beam cross-section increase with increasing distance a from the image plane 45. The illumination strength within the beam 39 is, therefore, largest in the image plane 45 and continuously decreases with increasing distance a from the image plane 45. For this, the illumination strength is the light power per unit area traversing the beam cross-section and may, for example, be represented in units of watts per square meter.

The measurement module 41 comprises a light detector 47 having a light sensitive substrate 49. The beam 39 incident onto the light sensitive substrate 49 generates an electric signal at outputs 50 of the light detector 47 wherein the electric signal represents the light power incident onto the light sensitive substrate 49.

In the illustrated embodiment, an aperture 51 is disposed in the beam path before the light sensitive substrate 49 wherein the aperture 51 has an opening 52 having a diameter d being smaller than the diameter D of the beam 39 in the image plane 45 or being equal to the diameter D of the beam in the image plane 45. The cross-section area of the opening 52 having the diameter d is smaller than the surface of the light sensitive substrate 49 and, therefore, defines the effective detection area of the light detector 47. As the detection cross-section of the light detector 47 is smaller than the cross-section of the beam 39, the light power detected by the light detector 74 represents the illumination strength of the beam 39 at the position along the longitudinal axis of the beam 39 at which the light sensitive substrate 49 is disposed.

A schematically illustrated drive 53 is provided in order to displace the detector 47 in a direction of the beam 39, as indicated by an arrow 54 in FIG. 2. The drive 53 is controlled by a controller 55 also reading the detection signal of the detector 47 provided at the terminals 50. The controller 55 may vary the position of the light sensitive substrate 49 along the direction of the beam 39 by controlling the drive 53 and measure the illumination strength of the beam 39 in dependence of the position. Based on these thus obtained measurement data, i.e., the positions and the respective illumination strengths, it is possible to determine the position of the image plane 45 along the beam 39. This may be performed by using different conditions. For example, the position of the detection area 49 along the direction of the beam 39 may be varied until the detected illumination strength is at maximum. Then, the position of the light sensitive substrate 49 along the axis of the beam 39 coincides with the position of the image plane 45. As the position of the image plane 45 depends on the ametropia of the eye 3, in turn, the ametropia of the eye may be concluded based on the determined position of the image plane 45, and the controller 55 may output the corresponding measurement value representing the ametropia of the eye in dependence of the obtained position of the light sensitive substrate 49 at which the illumination strength is at a maximum.

However, other conditions are possible as well. For example, the controller 55 may dispose the light sensitive substrate 49 at multiple different positions along the axis of the beam 39 by controlling the drive 53 and measure the illumination strength at each position. Based on the measurement values and by using an appropriate calculation method, such as interpolation, it is possible to determine the position of the image plane 45.

In the example illustrated with reference to FIG. 2, the position of the detector 47 is displaced in the measurement module 41 in a direction of the beam 39. However, it is also possible to fixedly dispose the detector 49 in the measurement module 41 and to control a component of the optics 31 or another component in the beam path of the beam 39 in a way that the position of the image plane 45 relative to the measurement module and, therefore, relative to the light detector 47 changes. This may be performed by, for example, changing the position of the controlled component in the beam path and/or its refractive power. Again, it will be possible to determine the ametropia of the eye based on the obtained measurement values, i.e., the positions and refractive powers of the changeable components in the beam path, respectively, and the respective measured illumination strengths.

Figure 3:
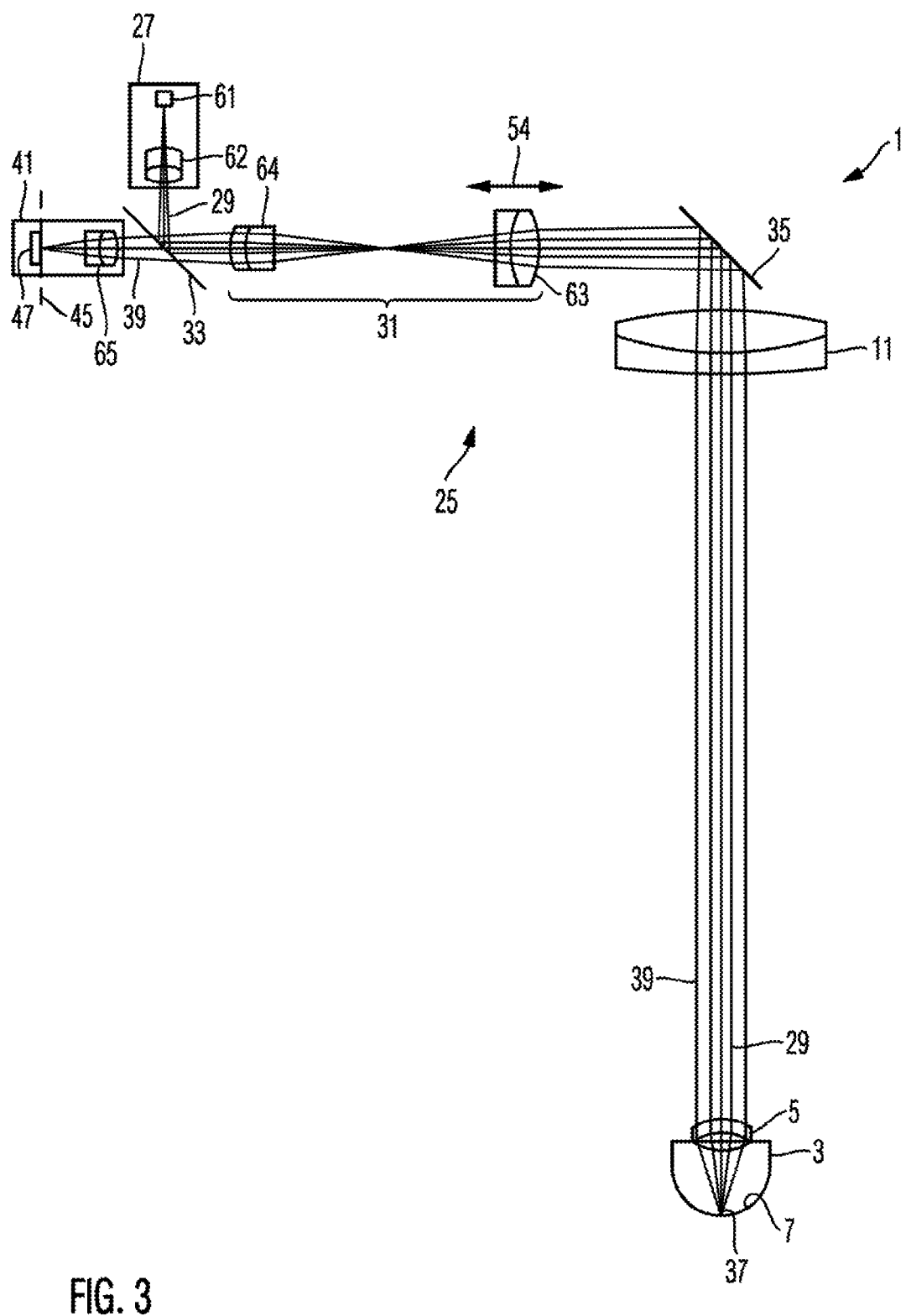
FIG. 3 shows a partial view of an eye surgery microscope according to a second embodiment.

FIG. 3 shows a schematic illustration of another example of an eye surgery microscope 1 wherein several essential components of the imaging beam path are not shown in FIG. 3 and merely those components relevant to the measurement beam path 25 are shown. A measurement light source 27 generates a measurement light beam reflected at a partially transparent mirror 33 and directed onto an eye 3 of a patient by optics 31, a mirror 35 and an objective lens 11 of the microscope 1. The measurement light beam 29 illuminates a spot 37 on a retina 7 of the eye 3. Measurement light reflected from the spot 37 is emitted from the eye 3 as a beam 39 provided to a measurement module 41 by the objective lens 11, the mirror 35, the optics 31 and the partially transparent mirror 33. The measurement light source 27 comprises a light source 61 and collimator optics 62. The measurement module 41 comprises optics 65 for generating an image of the retina 7 in a plane 45 wherein a light sensitive substrate of a light detector 47 is disposed in the plane 45. The optics 31 are configured as a Kepler telescope and comprises two groups of lenses 61 and 63. The group of lenses 63 is displaceable in a direction of the measurement light beam, as indicated by an arrow 54 in FIG. 3 by a drive not shown in FIG. 3.

The actual position of the image of the retina 7 within the measurement module 41 depends on the refractive forces of the lenses 65, 61, 63 and 11 in the beam path of the microscope 1, the refractive force of the eye lens 5 and the position of the lens 63 along the beam path. For different patient eyes 3 having different ametropias and refractive forces of the respective eye lens, a position of the lens 63 along the beam path may be found in a way that the image of the retina 7 is actually found in the plane 45 in which the light sensitive substrate of the detector 47 is disposed. For this, a controller may control the drive for displacing the group of lenses 63 in a direction 54 and read the detection signals of the detector 47 in order to determine the ametropia of the respective eye 3 as previously elucidated with reference to FIG. 2.

Figure 4A:
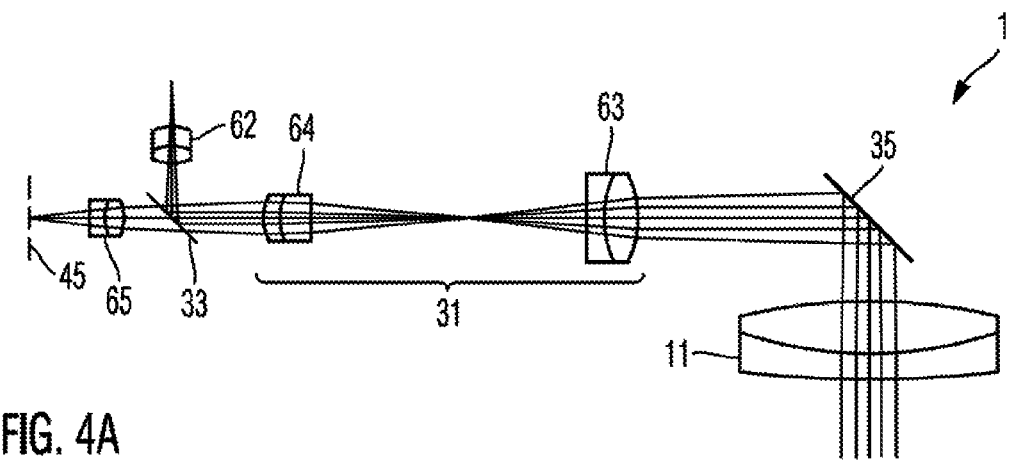
FIGS. 4A to 4C show schematic illustrations of beam paths in the eye surgery microscope shown in FIG. 3 for different ametropias.
Figure 4B:
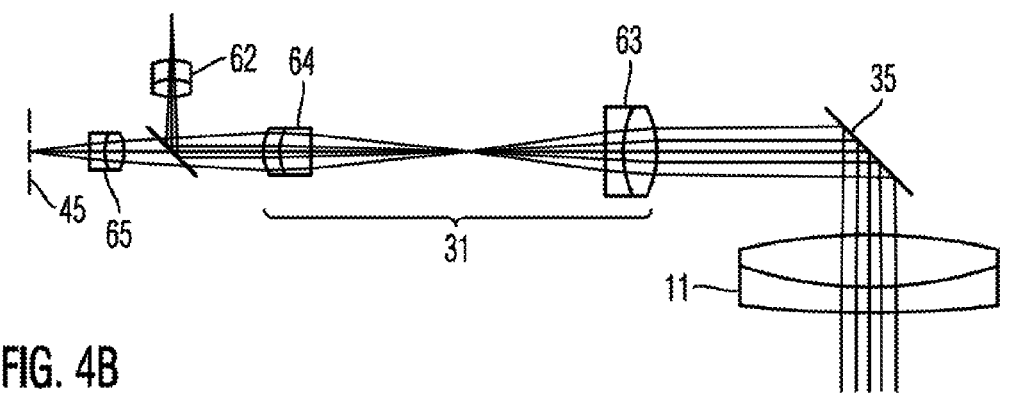
Figure 4C:
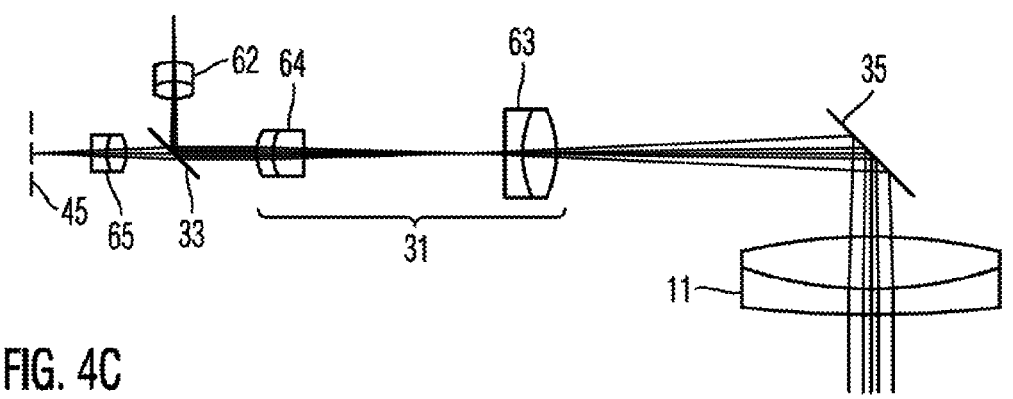

FIGS. 4A to 4C show magnified illustrations of the beam path of FIG. 3 of a different ametropias of the eye 3 wherein in each case the group of lenses 63 is disposed along the measurement beam path in a position so that the image of the retina 7 is formed in a fixed plane 45 within the measurement module 47. Here, FIG. 4A shows the beam path for a normal eye. FIG. 4B shows the beam path for a 3-diopter hyperopic eye and FIG. 4C shows the beam path for a 3-diopter myopic eye.

Figure 5A:
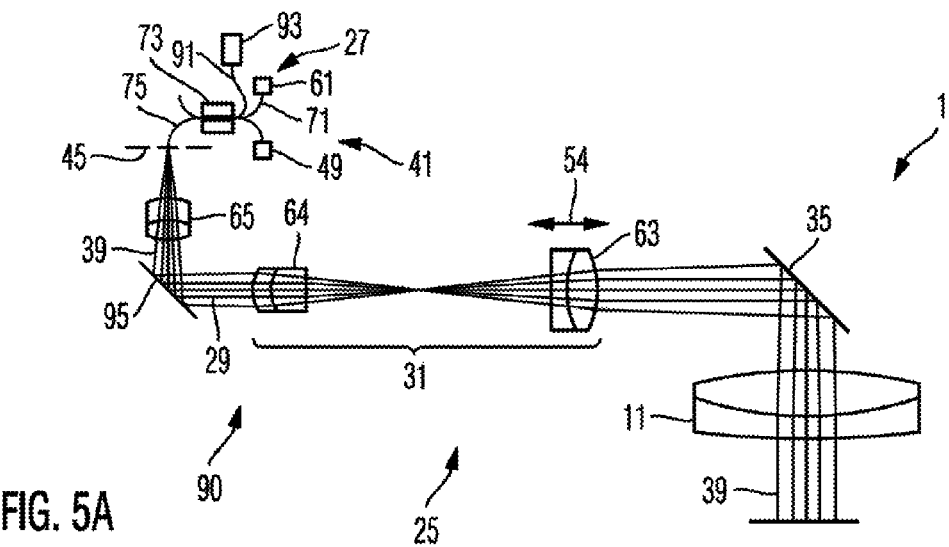
FIGS. 5A to 5C show schematic illustrations of beam paths in an eye surgery microscope according to a third embodiment for different ametropias.
Figure 5B:
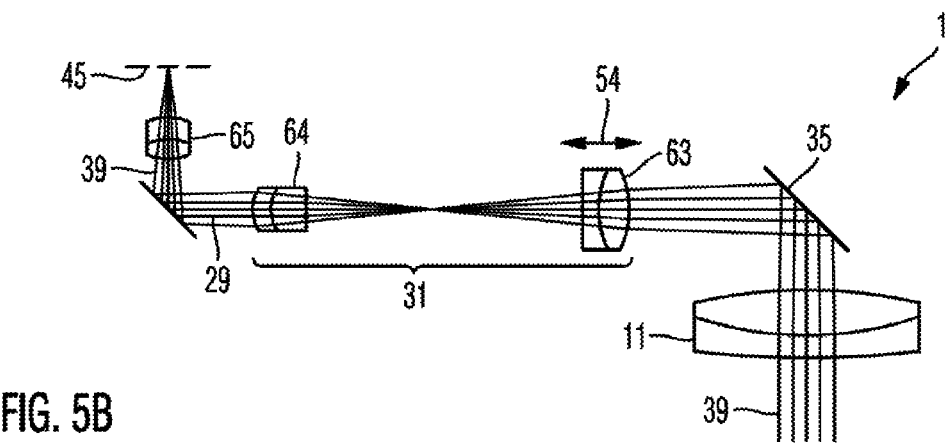
Figure 5C:
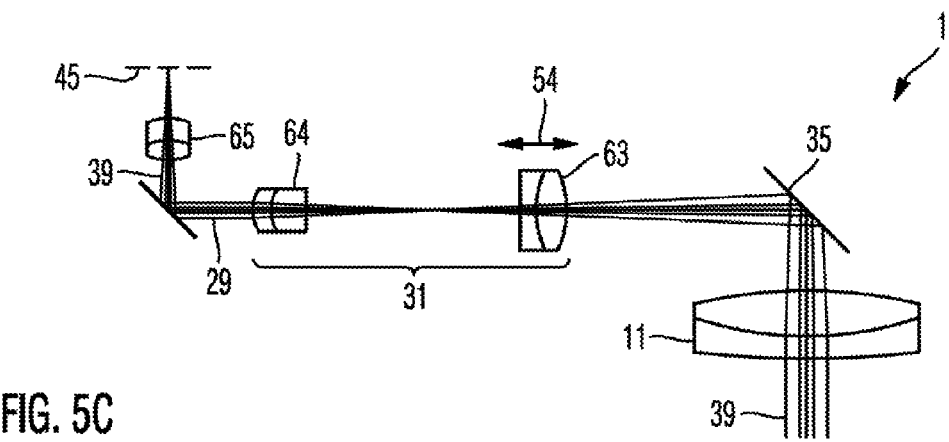

FIGS. 5A to 5C show another example of an eye surgery microscope 1 wherein merely details of the measurement beam path for different ametropiae according to FIGS. 4A to 40 are shown. Namely a normal eye in FIG. 5A a 3-diopter hyperopic eye in FIG. 5B and a 3-diopter myopic eye in FIG. 5C. The microscope shown in FIGS. 5A to 5C has a substantially similar configuration as the microscope elucidated with reference to FIGS. 3 and 4 wherein, in particular, optics 31 of the measurement beam path 25 are again configured as a Kepler telescope having two groups of lenses 64 and 63 and wherein the group of lenses 63 is displaceable in a direction 54 of the measurement beam path 25 by a drive.

The microscope 1 shown in FIGS. 5A to 5C differs from the previously elucidated examples essentially in that the measurement light source 27 and the measurement module 41 are integrated with one another by usage of light guides. A light source 61 generates measurement light and couples said measurement light into a glass fiber 71. A fiber coupler 73 couples light from the glass fiber 71 into a glass fiber 75 so that the light emerges as a measurement light beam 29 at a first end of the glass fiber 75, wherein the first end is disposed in a plane 45, and is directed onto an eye of the patient not shown in FIGS. 5A to 5C via the optics 31 and an objective lens 11 of the microscope 1. A beam 39 of measurement light leaving the eye is provided to the measurement module 41 via the objective lens 11 and the optics 31 wherein, as previously described, the group of lenses 63 is displaced in a direction 54 of the measurement light beam in a way that an image of the retina is formed in the plane 45. There, the light of the beam 39 enters the first end of the glass fiber 75, at the second end of which a light sensor 49 is disposed in order to detect the intensity of the measurement light coupled into the glass fiber 75. In this case, the cross-section of the first end of the glass fiber 75 defines the detection cross-section of the detector and the cross-section is smaller than the cross-section of the beam waist of the beam 39 in the plane 45.

As previously described, a controller may control a drive for displacing the group of lenses 63 to multiple positions and determine the illumination strength of the beam 39 in the plane 45 corresponding to the different positions by reading the light sensor 47 wherein the first end of the glass fiber 75 is disposed in the plane 45 in order to determine a value representing the ametropia of the measured eye based on these measurement values.

The eye surgery microscope 1 shown in FIG. 5A to 5C further comprises an optical coherence tomography apparatus 90 (OCT) in order to conduct measurements on the eye to be inspected using optical coherence tomography. For example, the OCT-apparatus 90 may serve to 3-dimensionally measure and display structures of the anterior chamber of the eye or the retina of the eye. The OCT-apparatus 90 comprises an interferometer having an interferometer device 93 having a reference path and a beam splitter in a way that a measurement path of the interferometer traverses parts of the optics of the eye surgery microscope 1 and extends to the region of the eye to be inspected using the OCT. For this, a glass fiber 91 emerges from the interferometer device 93 wherein the glass fiber 91 is a part of the measurement path of the interferometer and guides OCT measurement light towards the eye and, in turn, guides measurement light returning from the eye to the interferometer device 93. The OCT measurement light in the glass fiber 91 is coupled into the light guide 75 by the fiber coupler 73 or another fiber coupler provided for this so that the OCT measurement light may reach the eye through the group of lenses 65, the optics 31 and the objective lens 11 as was previously described for the measurement light beam 29. OCT measurement light returning from the eye again traverses the objective lens 11, the optics 31 and the group of lenses 65, enters into the light coupler 75 and is coupled into the glass fiber 91 via the fiber coupler 73 in order to enter into the interferometer device 93 and to be analyzed there for obtaining OCT measurement data using the OCT-apparatus 90.

For this, a mirror 95 at which the OCT measurement light is reflected may be configured as a scanning mirror, i.e., as a mirror pivotable in two linear independent spatial directions in order to displace the location at which the OCT measurement light is focused in the inspected region of the eye in a lateral direction of the OCT measurement light and, in this way, to obtain OCT measurement data from a spatially extended region. For this, it is also possible that instead of one mirror 95 two mirrors disposed after another in the beam path may be provided which are pivotable in two spatial directions, each of them being pivotable in a single spatial direction wherein one mirror performs the displacement of the beam in the one spatial direction and the other mirror performs the displacement of the beam in the other linearly independent spatial direction. The scanning mirror 95 of the OCT-apparatus 90 may also be used to position the spot on the retina of the inspected eye generated by the measurement light beam 29 at a desired position on the retina such as the fovea.

Figure 6A:
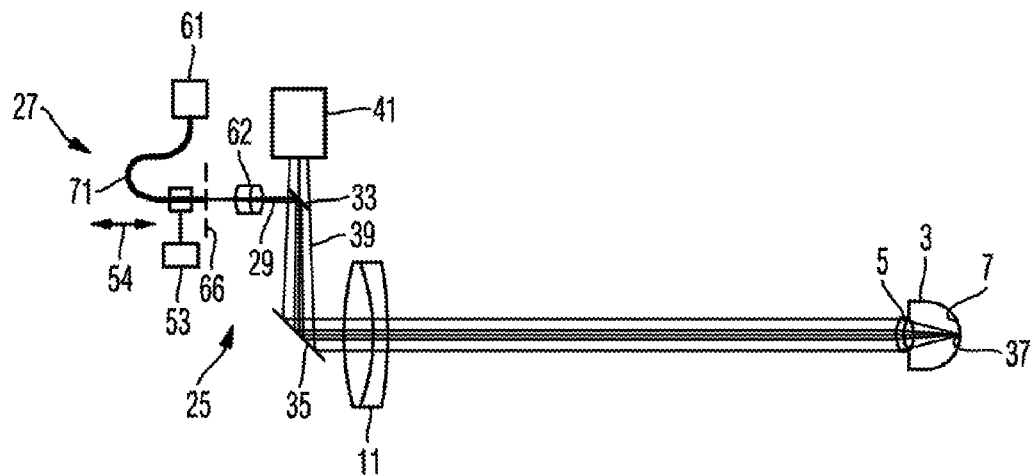
FIGS. 6A to 6C show schematic illustrations of beam paths in an eye surgery microscope according to a fourth embodiment for different ametropias.
Figure 6B:
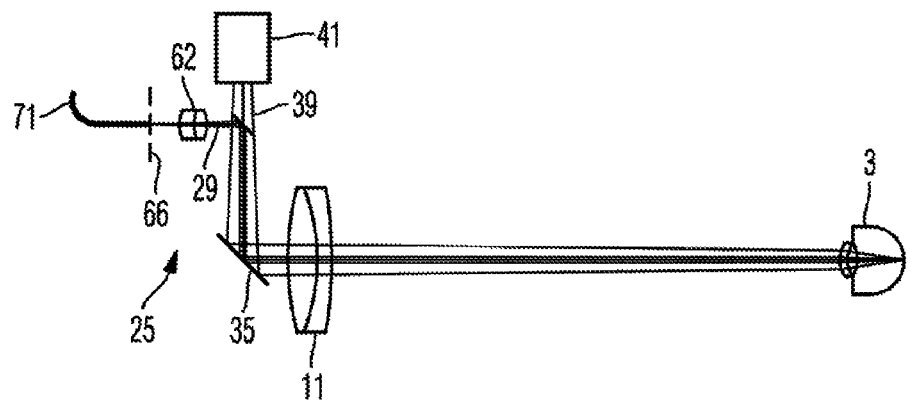
Figure 6C:
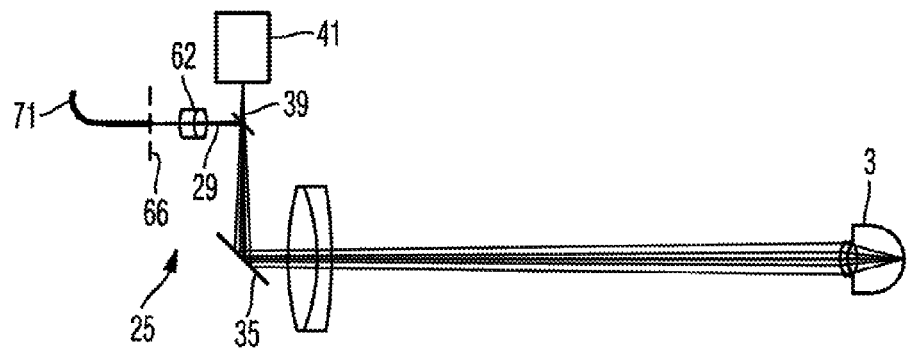

FIGS. 6A to 6C show another example of an eye surgery microscope 1, wherein again merely details of a measurement beam path 25 for different ametropias, namely a normal eye in FIG. 6A, a 3-diopter hyperopic eye in FIG. 6B and a 3-diopter myopic in FIG. 6C are shown. The microscope shown in FIGS. 6A to 6C essentially has a configuration similar to the microscopes elucidated with reference to FIGS. 3 to 5. In contrast to these microscopes, the microscope shown in FIGS. 6A to 6C does not have a changeable optics traversed by a measurement light beam 29 directed towards an eye 3 and a beam 39 of measurement light reflected at a retina 7 of the eye 3. However, this microscope 1 comprises a measurement module 41 configured to detect a position of an image of the retina along the direction of the beam 39. For this, the measurement module 41 may comprise optics for generating the image of the retina at last wherein a refractive power of the optics or positions of components of the optics are changeable in order to generate the image of the retina at a fixed position within the measurement module 41 wherein a light sensitive substrate of a detector may also be disposed at the fixed position or in order to vary a position of a light sensitive substrate along the direction of the beam 39 in order to detect the position of the image, as was previously elucidated several times.

A measurement light source 27 comprises a light source 61 generating measurement light and coupling said measurement light into a glass fiber 71 so that the measurement light is emitted from an end of the glass fiber 71 towards collimator optics 62 forming the measurement light beam 29. The end of the glass fiber 71 is disposed in a plane 66 and coupled to a drive 53 which may be controlled for displacing the end of the glass fiber 71 in a direction represented by an arrow 54 in FIG. 6A so that the distance of the end of the glass fiber 71 to the collimator optics 62 is changeable. By this distance, the divergence and convergence, respectively, of the measurement light beam 29 formed by the collimator optics 62 is also changeable and adaptable to the ametropia of the inspected eye 3 in order to illuminate a preferably small spot 37 on the retina 7 of the eye 3 using the measurement light beam 29.

With this, at a given position of the end 66 of the glass fiber 71 relative to the collimator optics 62, the ametropia of the eye 3 may be determined to a first approximation using the measurement module 41, then, the position of the end of the glass fiber 71 relative to the collimator optics 62 may be changed in dependence of the determined ametropia, and then, a more precise value of the ametropia of the eye may be determined using the measurement module 41. This process may be repeated iteratively, if necessary.

Furthermore, it is possible to fixedly set and maintain the position of the end of the glass fiber 71 relative to the collimator optics 62 if the diameter of the measurement light beam 29 formed by the collimator optics 62 is so small that the spots 37 on the retina 7 of the eye 3 illuminated by the measurement light beam 29 are sufficiently small for the considered ametropias of the eye.

Figure 7A:
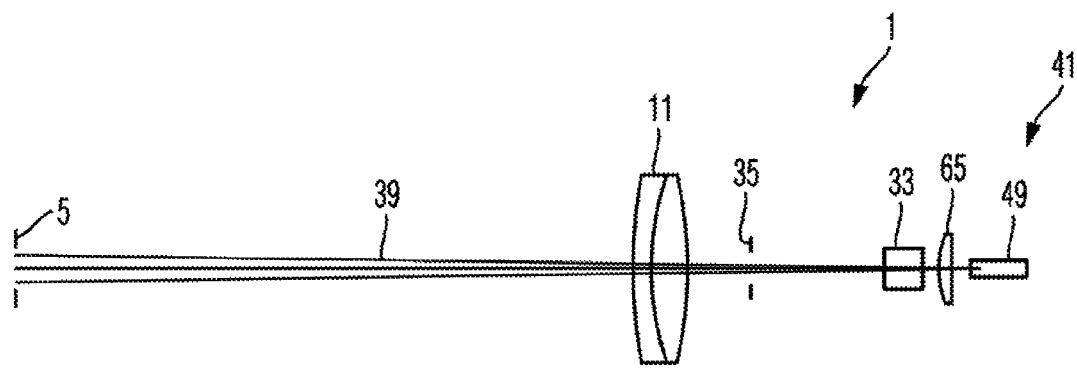
FIGS. 7A to 7C show schematic illustrations of beam paths in the meridional section in an eye surgery microscope according to a fifth embodiment for different ametropias.
Figure 7B:
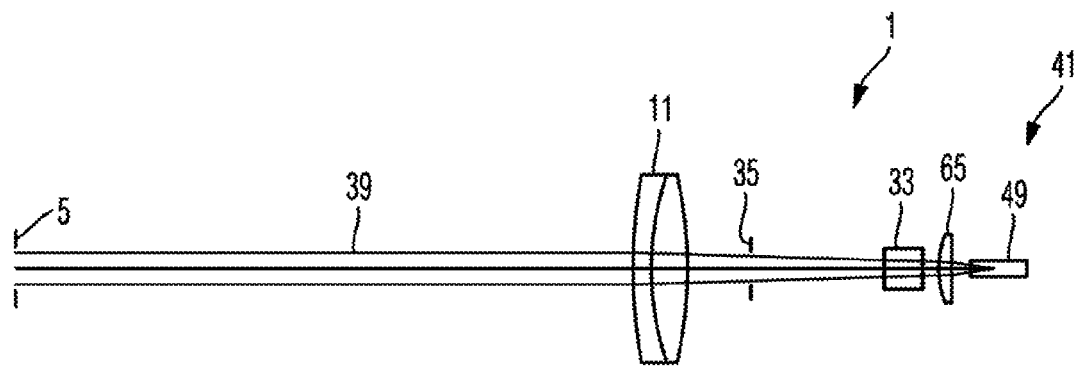
Figure 7C:
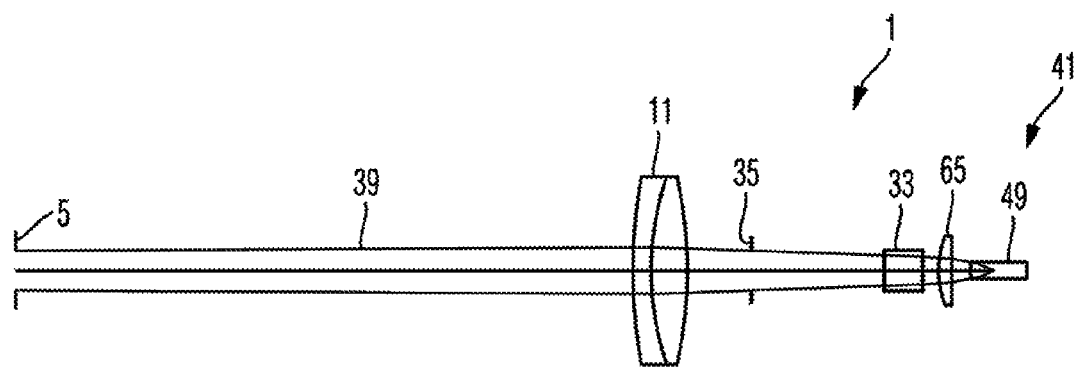
Figure 8A:
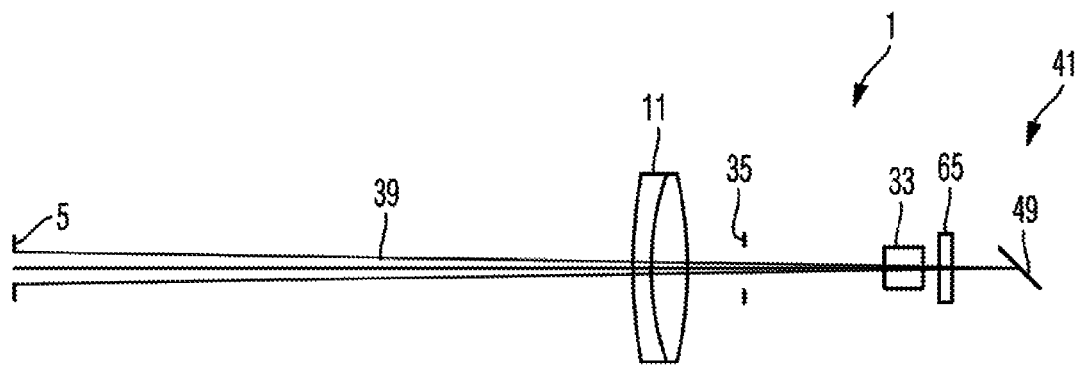
FIGS. 8A to 8C show schematic illustrations of beam paths in the sagittal section in the eye surgery microscope shown in FIGS. 7A to 7C for different ametropias.
Figure 8B:
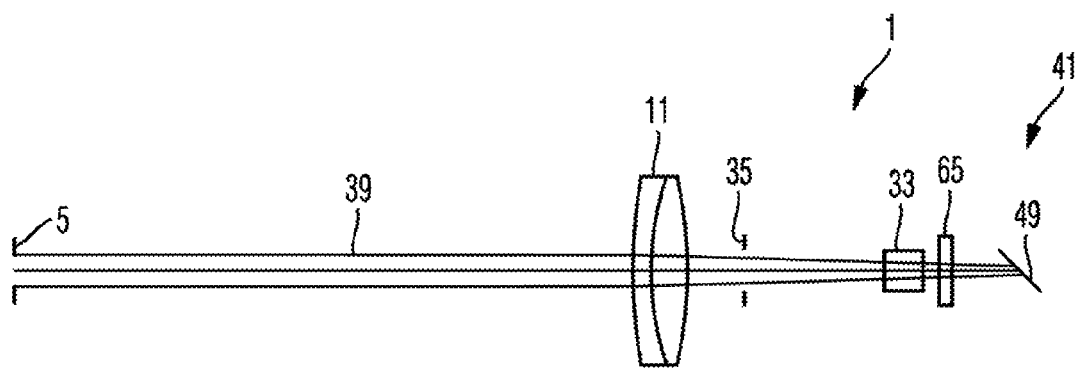
Figure 8C:
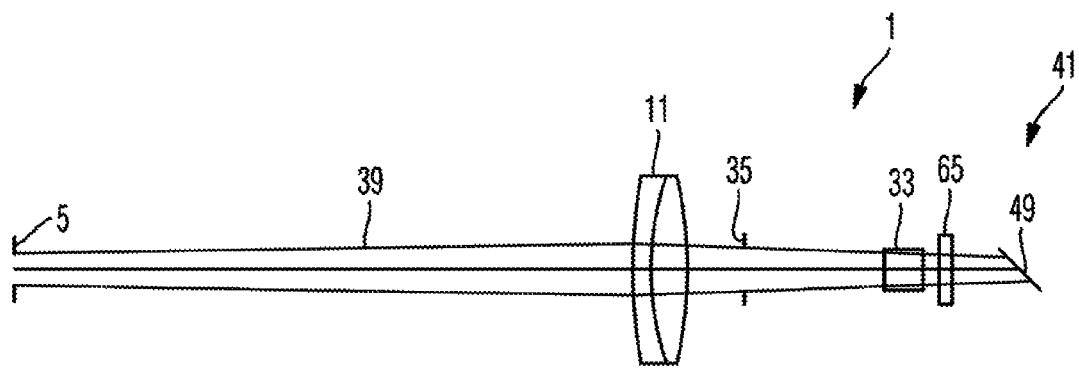

Another embodiment of an eye surgery microscope 1 is described hereinafter with reference to FIGS. 7A to 7C and 8A to 8C wherein FIGS. 7A to 7C show a meridional section of a measurement beam path and FIGS. 8A to 8C show a respective sagittal section of the measurement beam path and wherein the measurement beam path is shown for different ametropias of the eye, namely a 2.5 diopter myopic eye in FIGS. 7A and 8A, a normal eye in FIGS. 7B and 8B and a 2.5 diopter hyperopic eye in FIGS. 7C and 8C.

The microscope 1 shown in FIGS. 7A to 7C and 8A to 8C has a configuration similar to the configuration of the previously elucidated microscopes. FIGS. 7A to 8C essentially show the beam path of a beam 39 of measurement light reflected at the retina of an eye. The measurement light beam itself may be generated by a measurement light source not shown in FIGS. 7A to 8C, as previously described in the context of the microscopes elucidated with reference to FIGS. 1 to 6. The numeral 5 in FIGS. 7A to 8C refers to the position of a pupil of the inspected eye. The beam 39 of the measurement light leaving the eye traverses an objective lens 11 of the microscope, may be reflected at a mirror disposed at a position labeled with a numeral 35 and may traverse a beam splitter disposed at a position labeled with the numeral 33 before entering a measurement module 41. The measurement module 41 comprises allomorphic optics 55, which is a cylinder lens in the illustrated example, for generating a line focus. A light sensitive substrate 49 of a detector is disposed along this line focus in a way that a distance of the substrate 49 to the astigmatic optics 65 increases along the line of the line focus.

Figure 9:
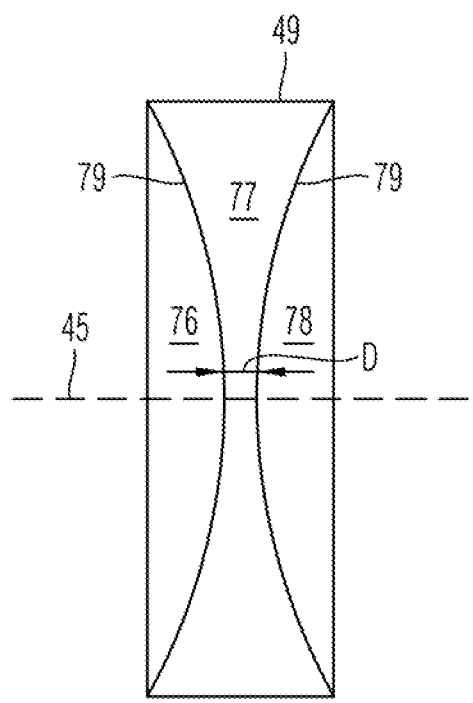
FIG. 9 shows a schematic illustration, of an illumination strength on a detector in a measurement module of the eye surgery microscope shown in FIGS. 7 and 8.

FIG. 9 shows a schematic illustration of an illumination strength of the beam 39 incident onto the substrate 49 of the detector. Three regions 76, 77 and 78 are separated from another by lines 79. In the regions 76 and 78, measurement light is not incident onto the substrate 49, whereas measurement light is incident onto the substrate 49 in the region 77. The region 77 has a changeable width in a longitudinal direction of the substrate 49 and is most narrow where a plane 45 oriented orthogonal to the optical axis and comprising the line focus intersects the area of the substrate 49. There, the illumination strength of the incident measurement light is also at maximum.

The substrate 49 may be configured as a two-dimensional array of pixels, the diameter of which is equal to or less than a smallest diameter D of the region 77 illuminated by measurement light on the surface of the substrate 49. The substrate 49 may further be configured as a one-dimensional array of multiple light, sensitive pixels disposed in a line along the direction of extension of the substrate 49. As the illumination strength is at maximum at the pixel and image element, respectively, where the plane 45, in which the image of the retina is formed, is disposed, the position of the plane 45 relative to the substrate 49 and, therefore, the ametropia of the eye may be concluded by evaluating the light intensities detected by the pixels.

FIGS. 10A to 10G show another example of an eye surgery microscope 1 wherein, again, merely details of a measurement beam path 25 are shown for different ametropias.

Figure 10A:
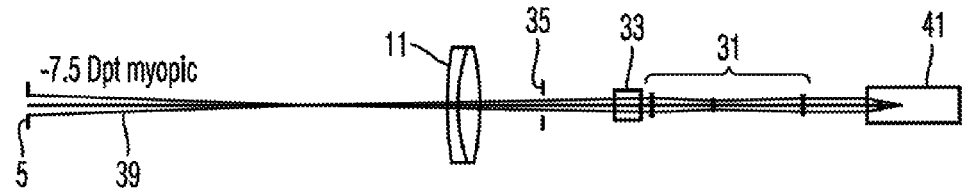
FIGS. 10A to 10G show schematic illustrations of beam paths in an eye surgery microscope according to a sixth embodiment for different ametropias.
Figure 10B:
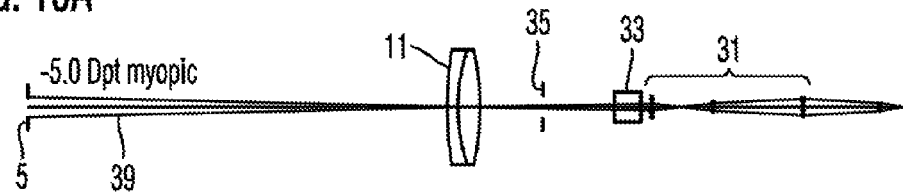
Figure 10C:
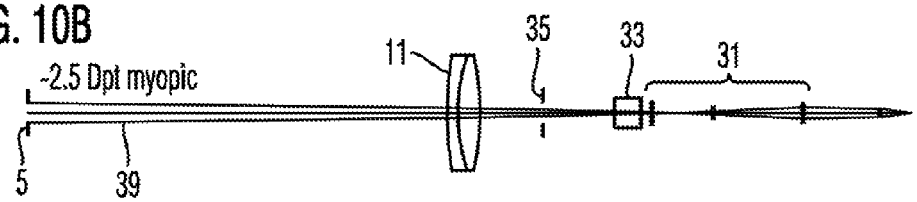
Figure 10D:
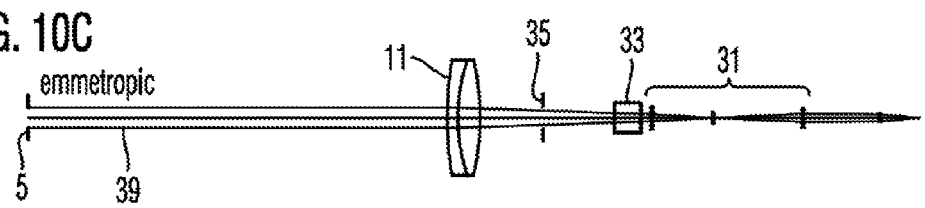
Figure 10E:
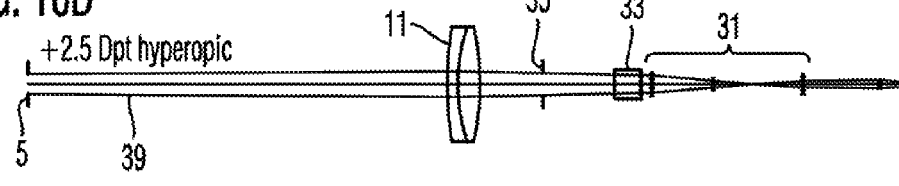
Figure 10F:
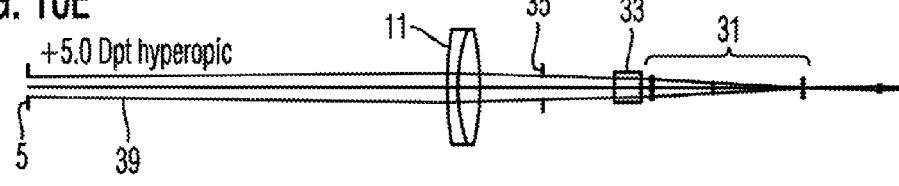
Figure 10G:
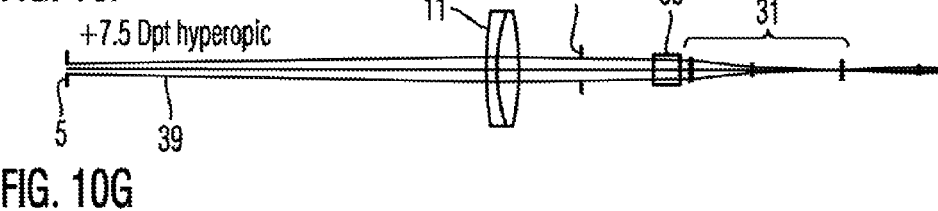
Figure 11A:
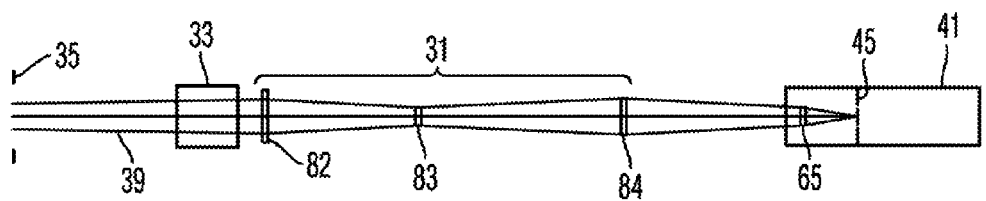
FIGS. 11A to 11G show details of the beam paths shown in FIGS. 10A to 10G.
Figure 11B:
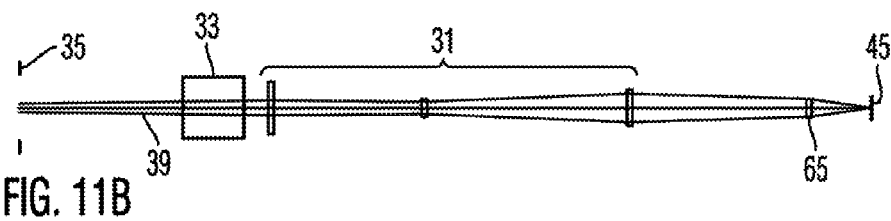
Figure 11C:
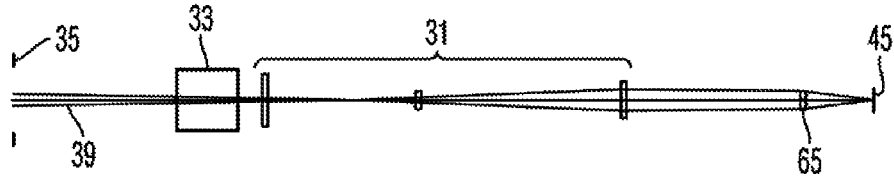
Figure 11D:
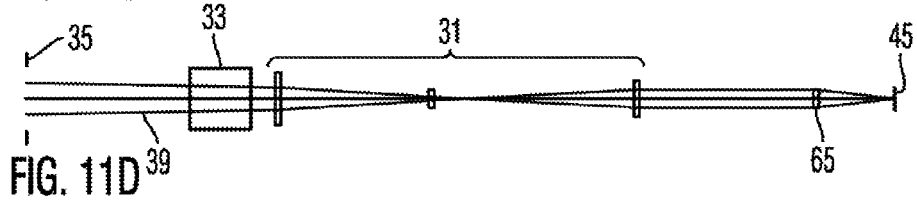
Figure 11E:
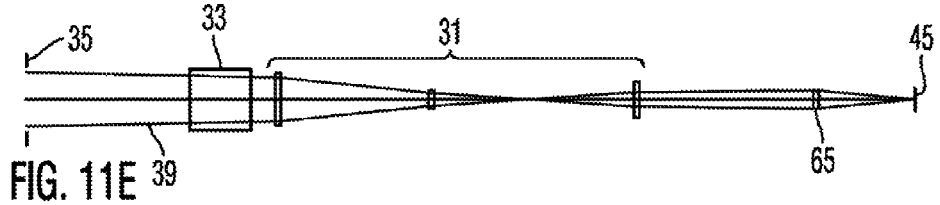
Figure 11F:
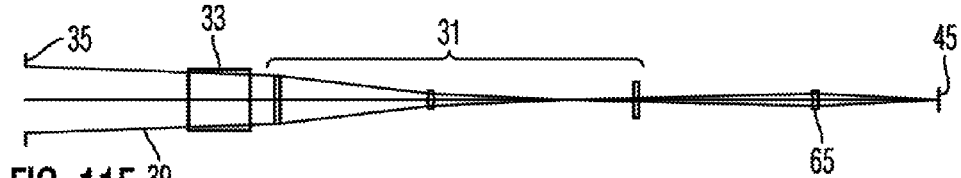
Figure 11G:
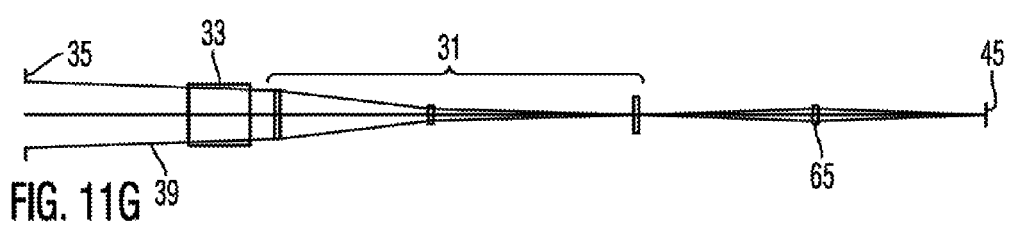
Figure 12A:
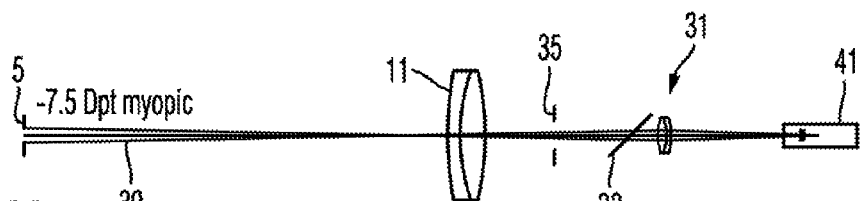
FIGS. 12A to 12C show schematic illustrations of beam paths in an eye surgery microscope according to a seventh embodiment for different ametropias.
Figure 12B:
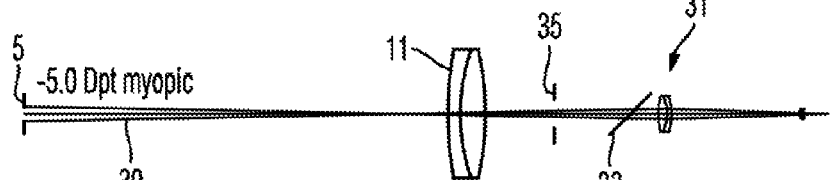
Figure 12C:
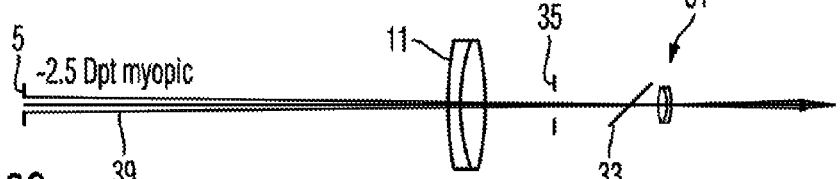
Figure 12D:
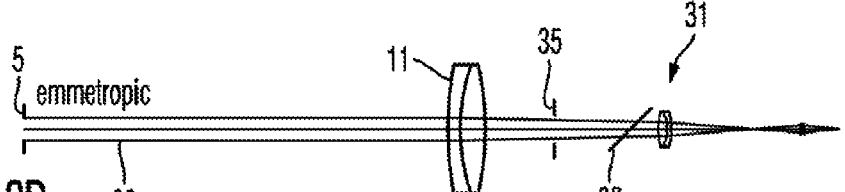
Figure 12E:
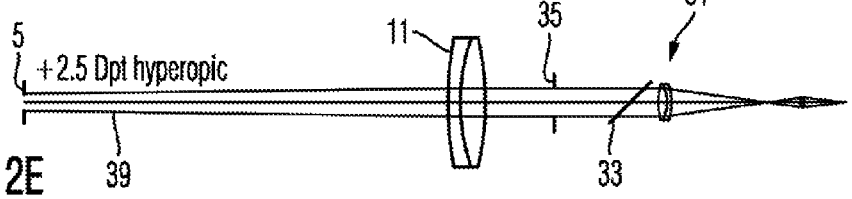
Figure 12F:
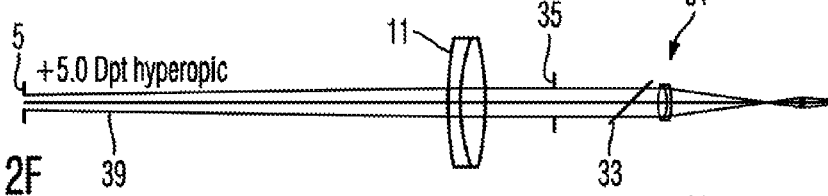
Figure 12G:
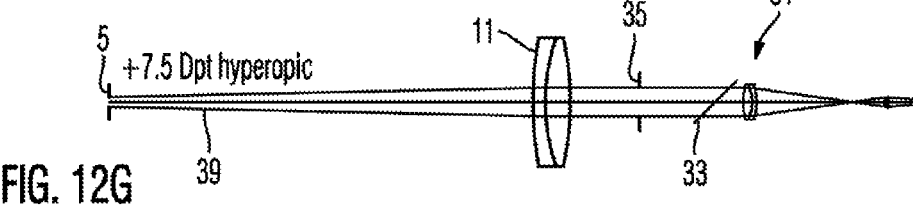
Figure 13A:
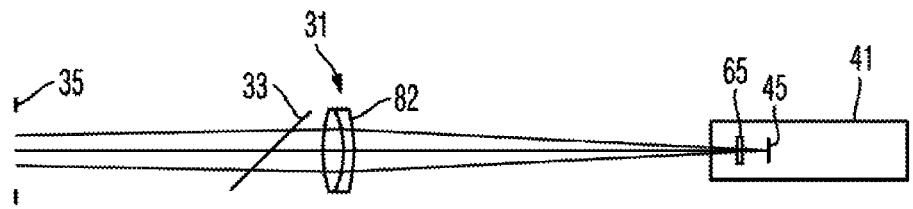
FIGS. 13A to 13G show details of the beam paths shown in FIGS. 12A to 12G.
Figure 13B:
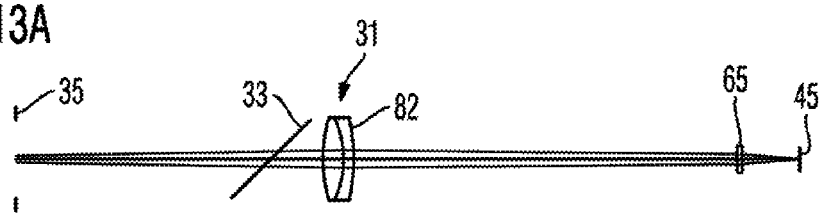
Figure 13C:
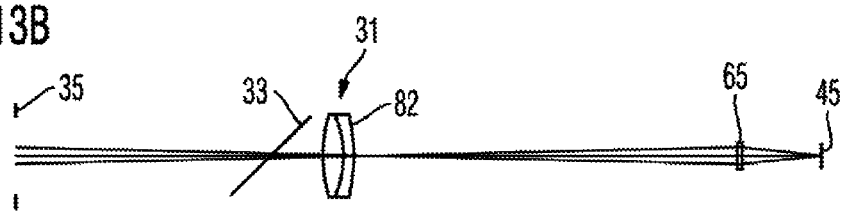
Figure 13D:
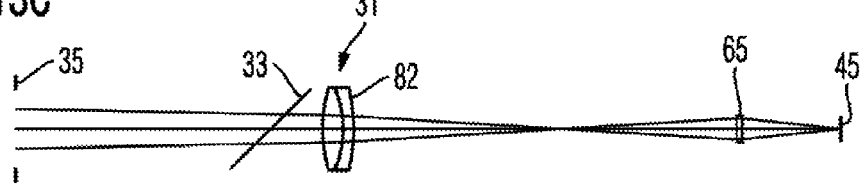
Figure 13E:
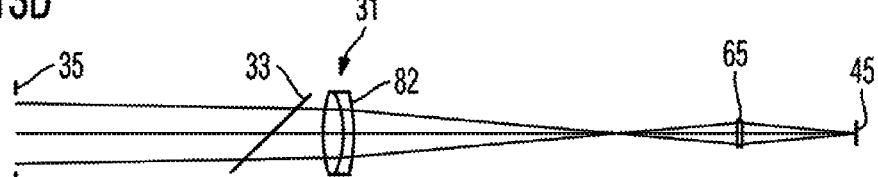
Figure 13F:
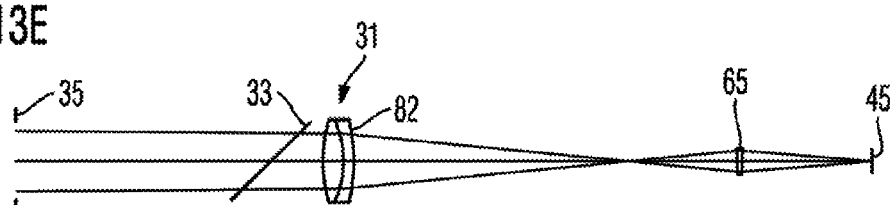
Figure 13G:
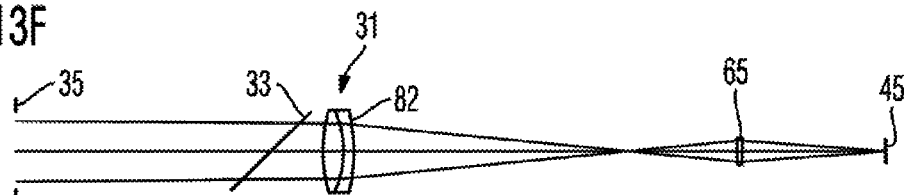

FIGS. 11A to 11G are magnified illustrations of parts of FIGS. 10A to 10G. FIGS. 10A and 11A show the beam path for a 7.5 diopter myopic eye, FIGS. 10B to 11B for a 5.0 diopter myopic eye, FIGS. 10C and 11C for a 2.5 diopter myopic, FIGS. 10D and 11D for a normal eye, FIGS. 10E and 11E for a 2.5 diopter hyperopic eye, FIGS. 10F and 11F for a 5.0 diopter hyperopic eye and FIGS. 10G and 11G for a 7.5 diopter hyperopic eye.

Details of the observation beam path of the microscope 1 and details for generating the measurement light beam are omitted in FIGS. 10A to 11G. These Figures merely illustrate the path of a beam 39 of measurement light leaving the eye towards a detector. The numeral 5 in FIGS. 10A to 10G refers to the position of a pupil of the inspected eye. The beam 39 of the measurement light leaving the eye traverses an objective lens 11 of the microscope 1, may be reflected at a mirror disposed at a position labeled with the numeral 35 and may traverse a beam splitter disposed at a position labeled with the numeral 33 before traversing optics 31 and entering a measurement module 41.

Optics 31 are configured so that an image of the retina of the inspected eye is formed in a plane 45 within the measurement module 41 for a large range of ametropias, namely from 7.5 diopter hyperopic to 7.5 diopter myopic. For this, optics 31 comprise a lens 82 having a focal length of +46 mm, a lens 83 having a focal length of −17 mm and a lens 84 having a focal length of +34 mm, and the measurement module 41 comprises a group of lenses 65 having a focal length of +15 mm for generating the image of the retina in the plane 45. The position of this plane 45 along the beam path of the beam 39 depends on the ametropia of the eye and may be determined according to a previously described technique. Accordingly, among others, the position of a light sensitive substrate along the beam path may be changed, the position of another optical component along the beam path may be changed or the refractive power of an optical component may be changed.

The optics 31 elucidated with reference to FIGS. 10A to 11G are special in that the optics 31 together with the objective lens 11 form an afocal system, the foci of which are located at infinity. Therefore, the beam path between the optics 31 and the measurement module 41 is a parallel beam path for a normal (emmetropic) eye and the pupil 5 of the eye of the patient is imaged onto the group of lenses 65 of the measurement module 41. With this, the advantage is obtained that a spatial region of finite extension exists for a predetermined measurement range of ametropias wherein no conjugated plane for the retina of the inspected eye is located in the spatial region. Hence, a position for a lens of positive refractive power and appropriate focal length may always be found so that a position of the image of the retina exists within the spatial region of finite extension for all ametropias of the measurement range wherein the light sensitive substrate of a detector may be disposed in the spatial region or wherein the spatial region may, in turn, be imaged onto a spatially fixed detector using changeable optics.

FIGS. 12A to 12G and 13A to 13G show, in correspondence with the previously elucidated FIGS. 10A to 10G and 11A to 11G, another example of an eye surgery microscope wherein, again, merely the beam path of a beam 39 of measurement light leaving the eye towards a measurement module 41 is shown. As in the case of the example described with reference to FIGS. 10A to 11G, optics 31 are also configured in the example shown in FIGS. 12A to 13G in a way that the retina is imaged into a plane 45 positioned in a handy finite range within the measurement module 41 for a large range of possible ametropias, namely from 7.5 diopter hyperopic to 7.5 diopter myopic. For this, the optics 31 merely comprise a group of lenses 82 and the measurement module 41 comprises a group of lenses having a focal length of +10 mm. The position of the image plane 45 within the measurement module depends on the ametropia of the inspected eye so that the ametropia of the eye may be concluded from finding the position of the image plane according to one of the previously elucidated methods.

The group of lenses 82 has a focal length of roughly +50 mm and is configured as a combined element of two individual lenses. The optical data of the group of lenses 82 are summarized in the table below.

| Area  | Radius [mm] | Thickness [mm] | Glass | Manufacturer |
|-------|-------------|----------------|-------|--------------|
| No. 1 | 31.059      | 3.5            | N-BK7 | Schott       |
| No. 2 | −21.909     | 1.5            | N-SF5 | Schott       |
| No. 3 | −62.869     |                |       |              |

Figure 14:
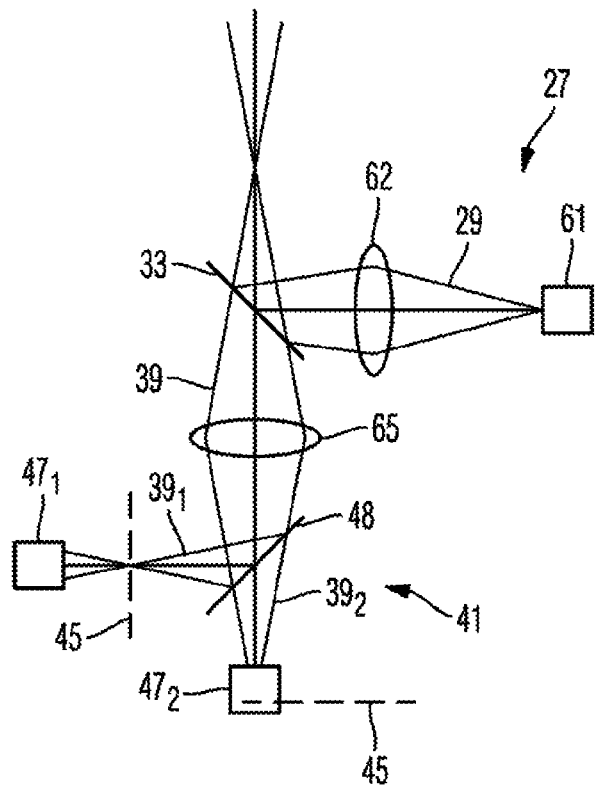
FIG. 14 shows a schematic illustration of further examples of a measurement module.

FIG. 14 shows another example of a measurement module 41 which may be used in an eye surgery microscope and which may be used instead of the measurement modules in the microscopes elucidated with reference to FIGS. 1 to 13.

The measurement module 41 shown in FIG. 14 serves to determine the position of an image of the retina of the eye generated by optics of the microscope along a measurement beam path. The measurement light may be generated by a measurement light source 27 having a light source 61 generating a measurement light beam 29 collimated by optics 62 and directed towards an eye of a patient not shown in FIG. 14 via a partially transparent mirror 33. Measurement light reflected at the retina of the eye traverses the partially transparent mirror as a beam 39 and is split into two partial beams $39_1$ and $39_2$ by a beam splitter 48. Each of the partial beams $39_1$ and $39_2$ generates an image of the retina in a plane 45. As previously described, the ametropia of the eye may be concluded from the position of the image along the measurement beam path. In the described example, two images 45 of the retina are generated via the beam splitter 48. A first detector $47_1$ is disposed in the partial beam $39_1$ in a way that the image 45 of the retina is disposed before the light sensitive substrate of the detector $47_1$ in the beam path. A second detector $47_2$ is disposed in the beam path of the partial beam $39_2$ in a way that its light sensitive substrate is disposed in the beam path before the plane 45 in which the image of the retina is formed. Therefore, the light sensitive substrate of the detector $47_1$ is disposed at a greater distance from the beam splitter 48 as the light sensitive substrate of the detector $47_2$. Both the detectors $47_1$ and $47_2$ are each configured to measure the illumination strength in the beam $39_1$ and $39_2$, respectively. For this, the detectors $47_1$, $47_2$ may comprise, for example, a substrate, the lateral extension of which is smaller than the diameter of the beams $39_1$, $39_2$ or an aperture may be disposed in front of each of the light sensitive substrates of the detectors $47_1$, $47_2$ wherein openings of the apertures have a diameter smaller than the diameter of the beams $39_1$, $39_2$ incident onto the apertures.

Each of the detectors $47_1$ and $47_2$ may be displaceable by a drive not shown in FIG. 14 in a direction of the beams $39_1$ and $39_2$, respectively. By controlling the drive, it is possible to position the detectors $47_1$ and $47_2$ in the beams $39_1$ and $39_2$ in a way that although the position of the planes 45 in which the image of the retina is formed is yet unknown, one of the detectors is disposed behind the plane 45 in the beam path and the other one of the detectors is disposed before the plane 45 in the beam path. This situation may be determined, for example, in that both detectors detect equal illumination strengths. Then, the plane 45 is located exactly between the positions of both the light sensitive substrates of the detectors $47_1$ and $47_2$ in the beam path.

Furthermore, it is possible to displace the detectors $47_1$, $47_2$ and the beam splitter 48 together as a group by a drive not shown in FIG. 14 in direction of the beam 39 for positioning the plane 45 in which the image of the retina is formed relative to the detectors $47_1$, $47_2$ in a way that is shown in FIG. 14, i.e., in the beam path of the beam $39_1$ before the detector $47_1$ and in the beam path of the beam $39_2$ behind the detector $47_2$. The ametropia of the eye may be concluded, as previously described, based on the position of the drive in which the situation is obtained.

The beam splitters comprised in the optics of the previously elucidated microscopes may be configured as polarizing beam splitters in order to avoid losses due to reflection in combination with polarizers and λ/4-plates. Furthermore, band pass filters may be employed for suppressing undesired stray light so that only wavelengths of a limited wavelength region are used for the measurement for determining the position of the image of the retina.

Furthermore the measurement light may be pulsed in time so that the spot on the retina of the eye is not permanently illuminated by a constant intensity in order to avoid unnecessary exposure to the retina. Furthermore, pulsed measurement light may also serve to obtain good measurement results by analyzing the temporal structure of the detected measurement light even though background light such as the ceiling illumination in an operating room is present.

With reference to FIGS. 7 to 8, a system was described having anamorphic optics having a cylinder lens. This system may be extended in that, for example, it has two anamorphic optics having, for example, two cylinder lenses, the line foci of which are oriented in mutually orthogonal directions. Then, it is possible to also determine an astigmatism of the inspected eye as a parameter of the measured ametropia.

While the disclosure, has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. A microscope for usage in eye surgery, wherein the microscope provides an imaging beam path for imaging a portion of an eye of a patient and a measurement beam path for measuring an ametropia of the eye of the patient, and wherein the microscope comprises:
    an objective lens traversed by the imaging beam path and having an object plane in which the eye of the patient is disposable;
    at least one of at least one ocular disposed in the imaging beam path behind the objective lens for generating an image of the object plane and a camera disposed in the imaging beam path behind the objective lens for detecting an image of the object plane,
    a measurement light source for generating a measurement light beam;
    a measurement module disposed in the measurement beam path and having at least one light detector detecting measurement light;
    optics traversed by the measurement beam path for directing the measurement light beam onto a retina of the eye of the patient and for providing measurement light reflected at the retina to the measurement module; and
    a controller;
    wherein the measurement module and the controller are configured to determine a position of an image of the retina along the measurement beam path, wherein the image of the retina is generated by the optics, and to output a measurement value representing the ametropia of the eye of the patient.

2. The microscope according to claim 1, further comprising a drive for displacing a position of at least one component disposed in the measurement beam path in a direction of the measurement beam path;
    wherein the at least one light detector provides a detection signal representing an illumination strength of the measurement light incident onto the at least one light detector; and
    wherein the controller is configured to control the drive in dependence of the detection signal until the illumination strength of the measurement light incident onto the at least one light detector fulfils a predetermined condition, and
    wherein the controller is configured to then output the measurement value representing the ametropia of the eye of the patient in dependence of an obtained position of the at least one component.

3. The microscope according to claim 2, wherein the predetermined condition is fulfilled if the illumination strength of the measurement light incident onto the at least one light detector is at maximum.

4. The microscope according to claim 2, wherein the measurement module comprises two light detectors disposed along the measurement beam path at different distances from the object plane, and
    wherein the predetermined condition is fulfilled if the illumination strengths of the measurement light incident onto the two light detectors have a predetermined ratio, and in particular are equal.

5. The microscope according to claim 2, wherein the component disposed in the measurement beam path and the position of which is displaceable by the drive comprises a lens of the optics traversed by the measurement beam path.

6. The microscope according to claim 2, wherein the component disposed in the measurement beam path and the position of which is displaceable by the drive comprises the at least one light detector.

7. The microscope according to claim 1, wherein the measurement module has a plurality of light detectors detecting the measurement light, wherein the light detectors of the plurality of light detectors are disposed along the measurement beam path at different distances from the object plane and wherein each of the light detectors of the plurality of light detectors provides a detection signal representing the measurement light incident onto the respective light detector; and
    wherein the controller is configured to output the measurement value representing the ametropia of the eye of the patient in dependence of the detection signals.

8. The microscope according to claim 7, wherein the measurement module comprises an astigmatic lens disposed in the measurement beam path before the plurality of light detectors.

9. The microscope according to claim 8, wherein the plurality of light detectors are disposed in a row.

10. The microscope according to claim 1, wherein the measurement light beam has in the object plane at least one of a diameter being less than 3.5 mm and a diameter greater than 0.5 mm.

11. The microscope according to claim 1, wherein the measurement beam path traverses the objective lens.

12. The microscope according to claim 11, further comprising a mirror disposed in the measurement beam path between the objective lens and the measurement module.

13. The microscope according to claim 1, further comprising a beam splitter disposed between the measurement light source and the object plane and in the measurement beam path between the object plane and the measurement module.

14. The microscope according to claim 1, wherein the at least one light detector has a detection cross-section being less than a diameter of a beam of measurement light incident onto the detection cross-section, reflected at the retina and provided to the measurement module.

15. The microscope according to claim 14, wherein the detection cross-section is defined by an aperture disposed in the measurement beam path before the at least one light detector.

16. The microscope according to claim 15, wherein the detection cross-section is defined by a first end of a glass fiber, the end being disposed in the beam of measurement light reflected at the retina and provided to the measurement module, wherein measurement light entering the glass fiber at the first end is guided to the at least one light detector by the glass fiber.

17. The microscope according to claim 16, wherein the measurement light source comprises the glass fiber and the measurement light beam is emitted from the glass fiber at the first end of the glass fiber.

18. The microscope according to claim 16, further comprising an optical coherence tomography system, wherein optical coherence tomography measurement light is emitted from the glass fiber at the first end of the glass fiber.

\* \* \* \* \*

UNITED STATES PATENT AND TRADEMARK OFFICE
CERTIFICATE OF CORRECTION

PATENT NO. : 9,615,740 B2  
APPLICATION NO. : 14/579053  
DATED : April 11, 2017  
INVENTOR(S) : Christoph Hauger et al.

It is certified that error appears in the above-identified patent and that said Letters Patent is hereby corrected as shown below:

In the Specification

Column 6, Line 6, "12C" should read --12G--.

Column 7, Line 42, "munch" should read --much--.

Column 9, Line 54, "40" should read --4C--.

Column 12, Line 25, "allomorphic" should read --anamorphic--.

Column 12, Line 26, "55" should read --65--.

Signed and Sealed this  
Sixth Day of June, 2017

Michelle K. Lee  
*Director of the United States Patent and Trademark Office*